US008404746B2

(12) United States Patent
Andary et al.

(10) Patent No.: US 8,404,746 B2
(45) Date of Patent: Mar. 26, 2013

(54) ANTI-DIABETES COMPOSITION CONTAINING CHICORIC ACID AND/OR ONE OF THE METABOLITES THEREOF

(75) Inventors: Claude Andary, Clapiers (FR); Gérard Ribes, Montpellier (FR); Didier Tousch, Montpellier (FR); Jacqueline Azay-Milhau, Saint Jean de Vedas (FR); Anne-Dominique LaJoix, Montpellier (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 691 days.

(21) Appl. No.: 12/310,209

(22) PCT Filed: Aug. 17, 2007

(86) PCT No.: PCT/EP2007/058580
§ 371 (c)(1),
(2), (4) Date: Aug. 5, 2009

(87) PCT Pub. No.: WO2008/022974
PCT Pub. Date: Feb. 28, 2008

(65) Prior Publication Data
US 2011/0015140 A1 Jan. 20, 2011

(30) Foreign Application Priority Data
Aug. 18, 2006 (FR) .................... 06 07382

(51) Int. Cl.
*A61K 31/19* (2006.01)
*A61K 31/045* (2006.01)
(52) U.S. Cl. .............. 514/557; 514/724; 514/866
(58) Field of Classification Search .......... 514/557, 514/724, 866
See application file for complete search history.

(56) References Cited

U.S. PATENT DOCUMENTS
| 2004/0043057 A1 | 3/2004 | Suzuki et al. |
| 2004/0192773 A1 | 9/2004 | Suzuki et al. |
| 2006/0069161 A1 | 3/2006 | Lee et al. |

FOREIGN PATENT DOCUMENTS
| DE | 1949822 | 4/1971 |
| EP | 1 559 421 A1 | 8/2005 |
| FR | 2638967 | 11/1988 |
| JP | 61-40763 | 2/1986 |
| WO | WO 00/15215 A1 | 3/2000 |
| WO | WO 00/47045 | 8/2000 |
| WO | WO 02/064536 A1 | 8/2002 |
| WO | WO 03/029183 A1 | 4/2003 |

OTHER PUBLICATIONS

Khan et al., "Safoof-e-Zyabites," Traditional Knowledge Digital Library, Second Edition, Formulation Id: NA4/2608, pp. 4-5, 1928.
Kabiruddin et al., "Qurs Tabasheer," Traditional Knowledge Digital Library, vol. II (Compiled), Formulation Id: MA3/476, pp. 7-8, 1938.
Sahib et al., "Salavallathagi," Traditional Knowledge Digital Library, Formulation Id: SR09/155, pp. 10-11, 1975.
Arzani et al., "Sharbat-e-Afsanteen Barae Elal-e-Jigar," Traditional Knowledge Digital Library, Formulation Id: MH5/1504C, pp. 13-14, 1968.
Khan et al., "Sharbat Buzoori Baarid," Traditional Knowledge Digital Library, Formulation Id: MH1/2190, pp. 16-17, 1921.
Khan et al., "Arq Zarishk," Traditional Knowledge Digital Library, Formulation Id: NA4/3442, pp. 19-20, 1928.
Qaadri et al., "Sherbet Barai Muqawwe-e-qalb," Traditional Knowledge Digital Library, Formulation Id: MH5/977, p. 22, 1968.
Khan et al., "Arq-e-kafoor," Traditional Knowledge Digital Library, Formulation Id: NA4/3446, pp. 24-25, 1928.
Reaven, Gerald M.,"Role of insulin resistance in human disease," *Diabetes*, Banting Lecture, Dec. 1988, vol. 37, pp. 1595-1607.
Ferrannini et al., "Hyperinsulinaemia: the key feature of a cardiovascular and metabolic syndrome," *Diabetologia*, 1991, vol. 34, pp. 416-422.
Alemzadeh et al., "Modification of Insulin Resistance by Diazoxide in Obese Zucker Rats," *Endocrinolgy*, Jan. 1993, vol. 133, No. 2, pp. 705-712.
Slover et al., "Prevention of type I diabetes and recurrent β-cell destruction of transplanted islets," *Endocrine Reviews*, Apr. 1997, vol. 18, No. 2, pp. 241-258.
Haffner, "Pre-diabetes, insulin resistance, inflammation and CVD risk," *Diabetes Res. and Clin Practice*, 2003, pp. S9-S18.
Catalano et al., "Gestational diabetes and insulin resistance: Role in short- and long-term implications for mother and fetus," *Metabolism*, 2003, pp. 1674S-1683S.
International Search Report issued on Sep. 8, 2008 for application No. PCT/EP2007/058580.
Nomura et al., "Synthesis of Amide Compounds of Ferulic Acid, and Their Stimulatory Effects on Insulin Secretion in Vitro," *Bioorganic & Medicinal Chemistry*, vol. 11, pp. 3807-3813 (2003).
Ohnishi et al., "Antioxidant activity and hypoglycemic effect of ferulic acid in STZ-induced diabetic mice and KK-A$^y$ mice," *BioFactors*, vol. 21, pp. 315-319 (2004).
Tagashira et al., "Cardiovascular disease medicine and health food," *Database WPI*, Nov. 10, 2005, p. 8, AN 2005-763566.
Chikuno et al., "Hypoglycemic agent," *Database WPI*, Sep. 25, 2002, p. 3, AN 2003-345667.
Jung et al., "Antihyperglycemic and Antioxidant Properties of Caffeic Acid in *db/db* Mice," *The Journal of Pharmacology and Experimental Therapeutics*, vol. 318, No. 2, pp. 476-483 (2006).
Hsu et al., "Caffeic Acid as Active Principle from the Fruit of *Xanthium strumarium* to Lower Plasma Glucose in Diabetic Rats," *Planta Medica*, vol. 66, pp. 228-230 (2000).

(Continued)

*Primary Examiner* — Kevin E Weddington
(74) *Attorney, Agent, or Firm* — Foley & Lardner LLP

(57) ABSTRACT

The present invention relates to the use of chicoric acid and/or at least one of these metabolites selected among mono-caffeoyl-tartaric acid and/or m-hydroxyphenylpropionic acid, and/or 4-vinylcatechol and/or 4-ethylcatechol for manufacturing a composition intended for prevention or treatment in an insulin-resistant patient or hypoinsulinemia and/or associated pathologies.

26 Claims, 5 Drawing Sheets

OTHER PUBLICATIONS

Figure 1:
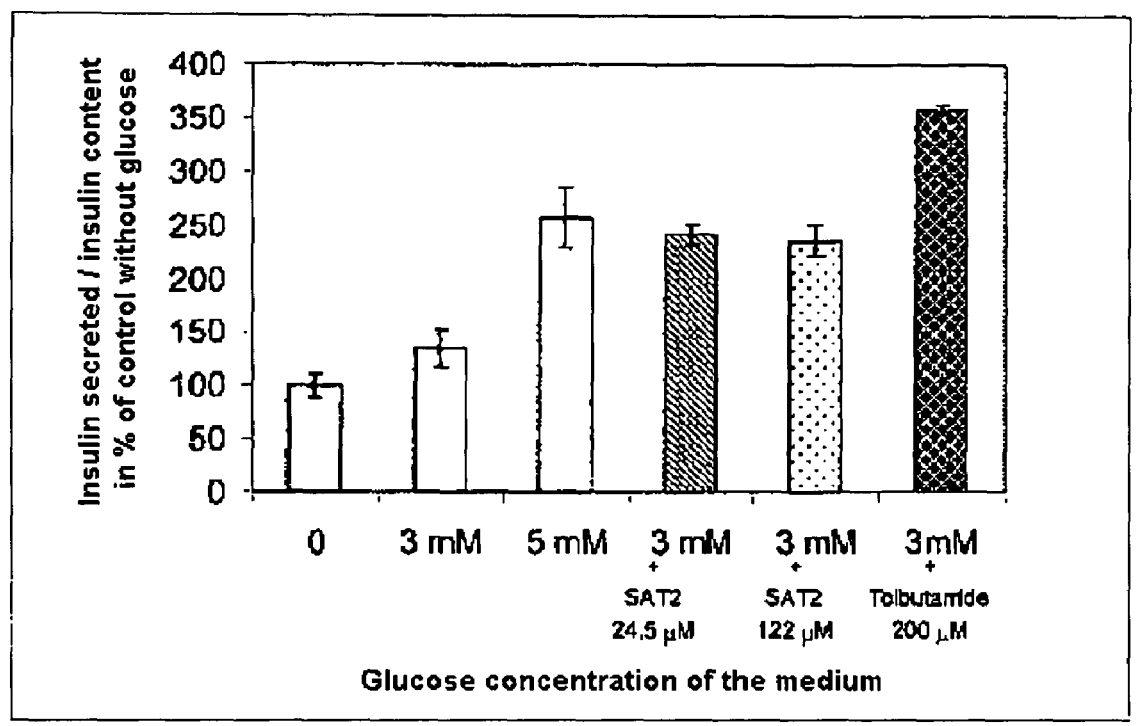

Fuwa et al., "Antidiabetic," *Database WPI*, Aug. 2, 1986, p. 7, AN 19860242356.

Kano et al., "Food Composition having inhibitory action on postprandial elevation of blood glucose," *Database WPI*, Apr. 22, 2003, p. 3, AN 2003-666734.

Matsui et al., "Anti-hyperglycemic Potential of Natural Products," *Mini-Reviews in Medicinal Chemistry*, vol. 6, pp. 349-356 (2006).

Stadler et al., "The inhibitory effects of coffee on radical-mediated oxidation and mutagenicity," *Mutation Research*, vol. 308, pp. 177-190 (1994).

Bailly et al., "Anti-HIV Activities of Natural Antioxidant Caffeic Acid Derivatives: Toward an Antiviral Supplementation Diet," *Current Medicinal Chemistry*, vol. 12, pp. 1811-1818, (2005).

Balasubashini et al., "Protective effects of ferulic acid on hyperlipidemic diabetic rats," *Acta Diabetol*, vol. 40, pp. 118-122 (2003).

Kim et al., "Lipid-lowering efficacy of hesperetin metbolites in high-cholesterol fed rats," *Clinica Chimica Acta*, vol. 327, pp. 129-137 (2003).

Broca et al., "4-Hydroxyisoleucine: experimental evidence of its insulinotropic and antidiabetic properties," *American Physiological Society*, pp. E617-E623 (1999).

Facino et al., "Echinacoside and Caffeoyl Conjugates Protect Collagen from Free Radical-Induced Degradation: A Potential use of Echinacea Extracts in the Prevention of Skin Photodamage," *Planta Med.*, vol. 61, pp. 510-514 (1995).

Hemmerle et al., "Chlorogenic Acid and Synthetic Chlorogenic Acid Derivatives: Novel Inhibitors of Hepatic Glucose-6-phosphate Translocase," *Journal of Medicinal Chemistry*, vol. 40, No. 2, pp. 137-145 (Jan. 17, 1997).

King et al., "Structure-Activity Relationships: Analogues of the Dicaffeoylquinic and Dicaffeoyltartaric Acids as Potent Inhibitors of Human Immunodeficiency Viurs Type 1 Integrase and Replication," *J. Med. Chem.*, vol. 42, pp. 497-509 (1999).

Lacy et al., "Method for the Isolation of Intact Islets of Langerhans from the Rat Pancreas," *Diabetes*, vol. 16, No. 1, pp. 35-39 (Jan. 1967).

Dalby-Brown et al., "Synergistic Antioxidative Effects of Alkamides, Caffeic Acid Derivatives, and Polysaccharide Fractions from Echinacea purpurea on in Vitro Oxidation of Human Low-Density Lipoproteins," *Journal of Agricultural and Food Chemistry*, vol. 53, pp. 9413-9423 (2005).

Scarpati et al., "Chicoric Acid (Dicaffeyltartic Acid): Its islolation from Chicory (*Chicorium intybus*) and Synthesis," *Tetrahedaron*, vol. 4, pp. 43-48 (1958).

Sekine et al., "Glucose-Induced Insulin Secretion in INS-1 Cells Depends on Factors Present in Fetal Calf Serum and Rat Islet-Conditioned Medium," *Diabetes*, vol. 46, pp. 1424-1433 (1997).

Zhao et al., "Facile Syntheses of (2R,3R)-(−)- and (2S,3S)-(+)-Chicoric Acids," *Synthetic Commnications*, vol. 28, No. 4, pp. 737-740 (1998).

Zimmet et al., "Global and societal implications of the diabetes epidemic," *Nature*, vol. 414, pp. 782-787 (Dec. 2001).

Claret et al., abstract, *Conference for The Society of Biomolecular Screening*, Sep. 11-15, 2004, Orlando, Florida.

ANTI-DIABETES COMPOSITION CONTAINING CHICORIC ACID AND/OR ONE OF THE METABOLITES THEREOF

This application is a U.S. national stage application of International application no. PCT/EP2007/058580, filed Aug. 17, 2007, which claims priority to French application no. 0607382, filed Aug. 18, 2006, all of which are hereby incorporated by reference in their entirety.

The present invention relates to an antidiabetic composition able to stimulate insulin secretion and thus to be used as a treatment for type 2 (non-insulin-dependent) diabetes.

It is recognized that diabetes currently affects millions of individuals worldwide. The number of diabetics will reach 300 million in 2025 (1). Consequently, diabetes constitutes a major public health problem.

There several types of diabetes mellitus, including:
type 1 diabetes, also known as insulin-dependent diabetes,
type 2 diabetes, also known as non-insulin-dependent diabetes.

Type 2 (non-insulin-dependent) diabetes is by far the most common (approximately 90% of cases). Formerly known as adult-onset diabetes, this type of diabetes occurs mainly in adults over 40 years presenting, in 80% of cases, with obesity or at least with excess weight. At the onset of the disease, pancreatic insulin production may be abnormally high or low.

Among patients with type 2 diabetes, two metabolic changes are the principal cause of an increase in glycemia (hyperglycemia):
1. An insulin (thus pancreatic) deficiency in the endocrine response to glucose.
2. A deficiency in the action of insulin (insulin resistance) in peripheral tissues, primarily muscles and adipose tissues (extra-pancreatic effect).

This change in the insulin response to glucose can thus be due to two causes according to the stage of the disease: either too little insulin secretion under the effect of glucose, or excessive insulin secretion in order to compensate for the decrease in its action on target tissues.

Type 2 diabetes is first treated by measures to improve health and diet, with the particular goal of losing excess weight. The following step is a pharmacological treatment with oral antidiabetics, which are substances that act by stimulating insulin secretion (insulin stimulators) in order to compensate for the deficiency. The principal insulin stimulators are the sulfonylureas and the glinides (which act principally on the ATP-dependent potassium channel).

The other therapeutic alternative is to improve the action of insulin (insulin sensitizers). Two groups of substances are recognized for this purpose, namely the biguanides (metformin) and the thiazolidinediones, also known as the glitazones (rosiglitazone, troglitazone, pioglitazone).

If all these fail, insulin replacement therapy may prove necessary to maintain normal glycemia.

The principal substances able to stimulate insulin secretion (insulin stimulators) are the hypoglycemic sulfamides (sulfonylureas) or related substances (glinides). However, these substances, which act primarily on the ATP-dependent potassium channels of pancreatic β cells, have a certain number of disadvantages.

Thus, depending on dosing and the patient's sensitivity, hypoglycemia due to excess insulin secretion can occur, particularly in the elderly. This can lead to insulin shock.

To remedy these disadvantages, researchers turned their attention toward other pharmacological alternatives that stimulate insulin by acting on targets other than ATP-dependent potassium channels, namely those that modulate insulin secretion according to circulating glucose levels, thus avoiding complications such as post-treatment hypoglycemia. In particular, the search for novel pharmacologically active molecules is increasingly directed toward natural substances, namely plant extracts (2).

Thus, this search for natural compounds has revealed phenolic compounds derived from caffeic acid, such as chlorogenic acid purified from a variety of plants.

Chlorogenic acid, which acts on the hepatic (thus extra-pancreatic) level, is reputed to act on hepatic glucogenesis. Indeed, chlorogenic acid has a primarily hepatic inhibitory action on glucose-6-phosphatase (3), thus enabling better hepatic glucose uptake and thus better glucose tolerance. Chlorogenic acid does not act directly on the endocrine pancreas and thus is not an insulin stimulator but rather an insulin sensitizer that acts against insulin resistance in peripheral tissues.

Insulin resistance is the body's resistance to the hypoglycemic biological effects of insulin. As a result, these insulin sensitizing compounds are used for patients suffering from such a resistance to insulin.

However, no natural or synthetic phenolic substance derived from caffeic acid has yet been described as a stimulator of insulin secretion by pancreatic β cells.

The inventors of the present invention have extracted from plants, and purified, chicoric acid (dicaffeoyl-tartaric acid) of the following formula:

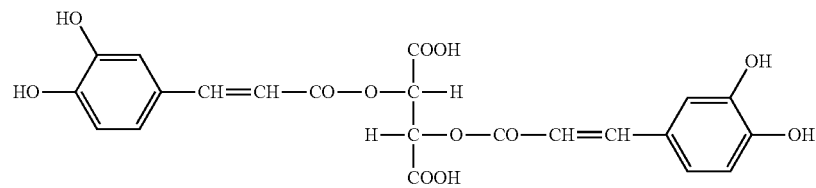 [SMILES: O=C(C=Cc1ccc(O)c(O)c1)OC(C(=O)O)C(OC(=O)C=Cc1ccc(O)c(O)c1)C(=O)O]

Chicoric acid, which is a caffeic diester of tartaric acid, belongs to the category of natural combinations of hydroxycinnamic acids which possess numerous medicinal virtues such as antioxidant, antiviral or anti-cancer activities (4, 5, 6). These combinations, originally purified from coffee and particularly rich in cinnamic derivatives, have been widely studied. Chicoric acid can be in the form of three isomers according to the isomerism of the tartaric acid: dicaffeoyl-(2S,3S)-(+)-tartaric acid, dicaffeoyl-(2R,3R)-(−)-tartaric acid and dicaffeoyl-meso-tartaric acid (7).

Chicoric acid is present in a number of plant species, more particularly those belonging to the following families: Fabaceae, Asteraceae, Lamiaceae, Equisetaceae or Potamogetonaceae or others, such as for example chicory (*Cichorium intybus*), echinacea (*Echinacea purpurea*), peanut (*Arachis hypogaea*), horsetail (*Equisetum arvense*), dandelion (*Taraxacum officinalis*), lettuce (*Lactuca sativa*) or Mediterranean seagrass (*Posidonia oceanica*). It is often the majority compound of all the species and plant families mentioned above, which thus can serve in the extraction and purification of this substance.

Chicoric acid can thus be isolated and purified from plants as described above. An example of the method for producing and isolating natural chicoric acid from wild chicory (*Cichorium pumilum, C. endivia* or *C. intybus*) is given below.

After drying and crushing, the chicory powder is extracted by boiling water for 20 minutes. After cooling, the extract is concentrated under vacuum at a temperature between 30° C. and 40° C. This new extract is deposited on an adsorbent column (Duolite S 761 or XAD 761 or other adsorbent of the same type) that was washed and activated beforehand. The first elution with slightly acidified water (pH 4) separates the sugars, organic acids and other small non-aromatic molecules while leaving adsorbed the aromatic organic molecules with phenolic or carbonylic functions. The latter are taken off with an 80:20 mixture of ethanol and water. The extracts obtained, enriched in chicoric acid, are concentrated and lyophilized.

This molecule is purified from the lyophilized powder by medium pressure liquid chromatography (MPLC) on a cellulose column. The eluting solvent is 0.10% or 0.15% acetic acid in water. The fractions richest in chicoric acid are combined and concentrated and this extract is purified by chromatography on a Fractogel TSK RW 40 (F) column. Elution is then carried out by water followed by a gradient of ethanol in water. The fractions containing pure chicoric acid are lyophilized.

Other methods for obtaining chicoric acid are described in Scarpati et al. (8), "Chicoric acid (dicaffeyltartaric acid): Its isolation from chicory and synthesis" Tetrahedron, 1958, vol. 4, pp. 43-48 for obtaining natural chicoric acid, or in application WO03/029183 for obtaining synthetic chicoric acid.

Surprisingly and unexpectedly, the inventors have shown that chicoric acid extracts from plants have insulin stimulating properties, unrelated to ATP-dependent potassium channels, and have obtained significant results in preventing and treating diabetes, in particular non-insulin-dependent diabetes. Indeed, the insulin stimulating effect of chicoric acid has been described by in vitro experiments on the INS-1E cell line and on islets of Langerhans isolated from rat pancreas and by in vivo experiments in normal rats. The results obtained on the INS-1E cell line show that the effect of chicoric acid very quickly reaches a maximum of stimulation, lower than the stimulation values obtained using a sulfonylurea drug such as tolbutamide known for its action on the ATP-dependent potassium channels of pancreatic β cells. This result suggests that chicoric acid probably does not act on this channel. Moreover, recent experiments by the inventors on islets of Langerhans isolated from rat pancreas have shown that the insulin stimulating effect of chicoric acid is dependent on the concentration of glucose. Chicoric acid can thus be a good, innovative alternative in the prevention and treatment of hypoinsulinemia, in particular related to diabetes, because it is able to stimulate insulin secretion without causing hypoglycemia in the patient as sometimes happens in patients treated with sulfonylureas, a situation that can be dangerous notably in the elderly.

In addition, we are reminded that one of the principal risk factors for triggering type 2 diabetes is excessive weight gain often related to sedentary lifestyle and/or imbalanced diet, which are disturbing new societal concerns for the industrialized nations. Obesity indeed contributes to the development of insulin resistance, i.e., when the action of insulin on extrapancreatic target tissues (muscles, liver) is decreased, glucose uptake by these tissues is highly altered. Insulin resistance is very often followed by compensatory hyperinsulinemia. This results from a relative incapacity of the plasma membrane to recruit glucose transporter cells, essentially GLUT4 for muscle and adipose tissues. This causal relationship between obesity and type 2 diabetes has taken shape as a major phenomenon in the field of public health. A body of evidence links hyperinsulinemia to the risk of strokes and helps draw a picture of metabolic syndrome or Reaven's syndrome X (insulin resistance, hyperinsulinemia, hypertriglyceridemia, arterial hypertension) and the morbidity risks associated with it.

In addition to the insulin stimulating properties of chicoric acid, the inventors have shown the stimulative effect of chicoric acid on glucose uptake at a dose that stimulates insulin, in particular on muscle tissues (the principal glucose uptake tissues in the body), and thus the insulin sensitizing effect of chicoric acid.

Chicoric acid can thus be a good, innovative alternative in the prevention and treatment of insulin resistance.

Thus, the present application describes an insulin stimulating composition characterized in that it comprises, as active substance, at least chicoric acid and/or a metabolite thereof.

Advantageously, the chicoric acid or metabolite thereof is in the form of a (+), (−) or meso isomer of dicaffeoyl-tartaric acid.

Advantageously, the metabolite of chicoric acid is monocaffeoyl-tartaric acid, caffeic acid, tartaric acid, ferulic acid, dihydrocaffeic acid, m-hydroxyphenylpropionic acid, dihydroxyphenylacetic acid, 4-vinylcatechol or 4-ethylcatechol.

One object of the present invention relates to the use of chicoric acid and/or at least one metabolite thereof chosen among monocaffeoyl-tartaric acid and/or m-hydroxyphenylpropionic acid, and/or 4-vinylcathecol and/or 4-ethylcatechol to manufacture a composition to prevent or treat in a subject insulin resistance or hypoinsulinemia and/or associated pathologies.

Preferably, the inventive use is characterized in that the composition is insulin stimulating and in that it is to prevent or treat hypoinsulinemia.

According to the present invention, "hypoinsulinemia" means an insulin deficiency in the affected subject, i.e., an abnormally low concentration of insulin in the subject's blood. Hypoinsulinemia can cause hyperglycemia in the affected subject.

Preferably, these pathologies related to insulin resistance or hypoinsulinemia according to the present invention are selected from a group comprising diabetes, dyslipidemia, in particular hyperlipidemia and hypertriglyceridemia, metabolic syndrome, arterial hypertension and obesity.

According to the present invention, "metabolic syndrome" means the pathology also referred to as syndrome X or Reaven's syndrome X.

Metabolic syndrome is a pathology defined by a set of risk factors including dyslipidemia (low HDL-C level, high triglyceride level), increase in abdominal circumference/obesity, but also insulin resistance (fasting hyperglycemia) and arterial hypertension. This syndrome affects millions of people worldwide, exposing them to a greater risk of developing diabetes with its complications of renal failure and retinopathy, or to cause a cardiovascular disease such as coronary artery disease, coronary insufficiency, myocardial infarction, angina, atherosclerosis, arteriosclerosis, cerebral vascular accident, thrombosis, atherothrombosis or glaucoma, or a hepatic disease such as steatosis, nonalcoholic steatohepatitis or nonalcoholic fatty liver disease.

Preventing and treating metabolic syndrome in at-risk patients can help decrease the appearance of cardiovascular diseases, type 2 diabetes or hepatic diseases.

The definition of metabolic syndrome is not a universal standard: that given by the National Cholesterol Education Program (NCEP, USA), as established by Adult Treatment Panel III, and selected for the present invention, includes the criteria listed in table 1 below. Patients have metabolic syndrome when they meet at least 3 of the 5 criteria indicated: increase in abdominal circumference, obesity, dyslipidemia, arterial hypertension, and hyperglycemia.

TABLE 1

| | ATP III |
|---|---|
| | Waistline: |
| Abdominal circumference | Men > 102 cm |
| | Women > 88 cm |
| | Triglycerides (TG): |
| Lipids | ≧150 mg/dl |
| | High density lipoprotein-cholesterol (HDL-C): |
| | Men > 40 mg/dl |
| | Women > 50 mg/dl |
| Blood pressure | ≧130/85 mmHg |
| Fasting glucose | ≧110 mg/dl |

Dyslipidemia is defined by a rise in triglycerides and low density lipoprotein-cholesterol (LDL-C), by a low concentration of high density lipoprotein-cholesterol (HDL-C), by an increase in the ratio total cholesterol/HDL-C and by the presence of small LDL particles. Dyslipidemia, often present in obese subjects, is also recognized as having an atherogenic profile, i.e., one which raises the risk of atheromatosis.

Preferably, the invention relates to the treatment or prevention of diabetes, in particular insulin-dependent diabetes or non-insulin-dependent diabetes, more preferentially non-insulin-dependent diabetes.

Moreover, as indicated above, the inventors have shown that the insulin stimulating effect of chicoric acid is dependent on the concentration of glucose. Thus, the insulin stimulating activity of the inventive composition is dependent on the concentration of glucose in the subject's blood.

Preferably, the inventive composition is insulin stimulating in a subject with a blood glucose concentration greater than 1 g/l.

Advantageously, the inventive composition is insulin sensitizing.

According to the present invention, "insulin sensitizing" means the properties of chicoric acid and metabolites thereof to prevent or treat insulin resistance, notably by activating nuclear insulin receptors in adipose and muscle cells. Such receptors are most notably PPARs (peroxisome proliferator-activated receptors).

Several mechanisms are involved in this insulin sensitizing action including, in particular, a decrease in various molecules involved in insulin resistance such as free fatty acids, leptin and TNF-α, molecules which oppose the action of insulin in cells.

Preferably according to the invention, the chicoric acid or metabolite thereof is of natural or synthetic origin.

More preferably according to the invention, the chicoric acid or metabolite thereof is of plant origin. Advantageously, the chicoric acid or metabolite thereof is obtained from plants belonging to the family of Asteraceae, Lamiaceae, Fabaceae, Equisetaceae or Potamogetonaceae, advantageously wild chicories (*Cichorium intybus*, for example) or cultivated chicories (chicory or endive, for example).

According to the present invention, "Asteraceae" refers to the family of Asteraceae (or Compositae) which is a family of dicotyledon plants. They are primarily herbaceous plants although trees, shrubs or lianas may be part of this family.

Preferably, the preferred genera in this family for obtaining the inventive chicoric acid are:
*Lactuca*: lettuces;
*Cichorium*: chicories (or endive);
*Cynara*: artichoke;
*Taraxacum*: dandelion;
*Tragopogon*: salsify;
*Echinacea*: echinacea;
*Lapsana*.

According to the present invention, "Lamiaceae" refers to the family of Lamiaceae (or Labiatae) which is a family of dicotyledon plants.

Preferably, the preferred genera in this family for obtaining the inventive chicoric acid are:
*Lavendula*: lavender;
*Orthosiphon aristus*: orthosiphon;
*Scutelleria*: skullcap;
*Teucrium*.

According to the present invention, "Fabaceae" refers to the family of Fabaceae (or Leguminosae) which is a family of dicotyledon plants. These are herbaceous plants, shrubs, trees or lianas.

Preferably, the preferred genera in this family for obtaining the inventive chicoric acid are:
Papilionoideae or Faboideae;
Caesalpinioideae;
Mimosoideae;
*Arachis hypogaea*: peanut.

According to the present invention, "Potamogetonaceae" refers to the family of Potamogetonaceae which is a family of monocotyledon aquatic plants.

Preferably, the preferred genus in this family for obtaining the inventive chicoric acid is:
*Posidonia*: seagrass.

According to the present invention, "Equisetaceae" refers to the family of Equisetaceae which is a family of pteridophytes. Preferably, the preferred genus in this family for obtaining the inventive chicoric acid is:
*Equisetum arvense*: horsetail.

The present application also describes the use of chicoric acid and/or a metabolite thereof for preparing a composition to stimulate insulin secretion in a diabetic subject.

The stimulation of insulin secretion leads to an improvement in glucose tolerance.

Accordingly, the present application also describes the use of said composition to improve glucose tolerance.

Moreover, stimulating insulin secretion and improving glucose tolerance make it possible to, among other things, prevent or treat diabetes, in particular non-insulin-dependent diabetes.

According to the present application, the chicoric acid or metabolite thereof used to prepare the composition to stimulate insulin secretion and to improve glucose tolerance to prevent and/or treat diabetes is in the form of a (+), (−) or meso isomer of dicaffeoyl-tartaric acid.

The present application describes that the chicoric acid or metabolite thereof used to prepare the composition to stimulate insulin secretion and to improve glucose tolerance to prevent and/or treat diabetes is of natural or synthetic origin.

The present application also describes that the chicoric acid or metabolite thereof used to prepare the composition to stimulate insulin secretion and to improve glucose tolerance and/or to prevent or treat diabetes is of plant or synthetic origin. Advantageously, the chicoric acid or metabolite thereof is obtained from Asteraceae, Lamiaceae, Fabaceae, Equisetaceae or Potamogetonaceae, advantageously from wild chicories (*Cichorium intybus*, for example) or cultivated chicories.

Preferably, the use of the inventive composition comprises the administration in the subject of 5-30 mg/kg of chicoric acid and/or less than 5-30 mg/kg of monocaffeoyl-tartaric acid and/or m-hydroxyphenylpropionic acid, and/or 4-vinylcathecol and/or 4-ethylcatechol and/or caffeic acid, and/or tartaric acid, and/or ferulic acid and/or dihydrocaffeic acid, per dose.

Another object of this application relates to a food composition characterized in that it comprises at least chicoric acid and/or a metabolite thereof.

The present application describes that the chicoric acid and/or metabolite thereof of the food composition is of natural or synthetic origin.

The present application describes that the chicoric acid and/or metabolite thereof of the food composition is of plant origin. Advantageously, the chicoric acid and/or metabolite thereof of the food composition is obtained from Asteraceae, Lamiaceae or Fabaceae, advantageously from the wild or cultivated chicories.

According to one aspect of the present invention, the composition is provided as a food composition characterized in that it comprises at least chicoric acid and/or at least one metabolite thereof chosen among monocaffeoyl-tartaric acid and/or m-hydroxyphenylpropionic acid, and/or 4-vinylcathecol and/or 4-ethylcatechol, and in that said composition is a food supplement.

According to the present invention, and according to the definition of Directive 2002/46/EC of the European Parliament and of the Council of Jun. 10, 2002, "food supplement" means foodstuffs the purpose of which is to supplement the normal diet and which are concentrated sources of nutrients or other substances with a nutritional or physiological effect, alone or in combination, marketed in dose form, namely forms such as capsules, pastilles, tablets, pills and other similar forms, sachets of powder, ampoules of liquids, drop dispensing bottles, and other similar forms of liquids and powders designed to be taken in measured small unit quantities. It should be noted that the present invention, intended for the global market, also includes the American definition of food supplement covering "any product intended to supplement a diet and which contains one or more specified dietary ingredients (vitamins, herb teas, plants, amino acids, a concentrate, an extract, a metabolite or any combination of said ingredients) in such as way as to increase its daily consumption".

According to another aspect of the invention, the inventive food composition is in the form of a nutraceutical.

The term "nutraceutical" refers to the active ingredient present in the natural state in a food which provides a beneficial effect on health. For example, allicin is a substance naturally present in garlic which has a protective antioxidant effect against cardiovascular diseases and cancer. Allicin is thus a nutraceutical in its natural state as well as when it is marketed in powder or tablet form. Concentrated broccoli tablets are another example of nutraceuticals.

The inventive food composition is in the form of a powder, capsule, tablet, solution, concentrate, syrup, suspension or dispersion. Preferably, the inventive food composition is in the form of a tablet, powder, capsule, pill or beverage.

Advantageously according to the invention, the food composition is added to a foodstuff.

Advantageously, the food composition is added during the preparation of the foodstuff, or right before consumption of the foodstuff. For example, the food composition is provided as a powder to sprinkle on a ready-to-eat foodstuff.

Preferably according to the invention, the food composition comprises 200-600 mg/l of chicoric acid and/or at least 200-600 mg of a metabolite thereof, in particular monocaffeoyl-tartaric acid and/or m-hydroxyphenylpropionic acid, and/or 4-vinylcathecol and/or 4-ethylcatechol, per dose and for a 60 kg individual.

Advantageously the food composition is characterized in that it comprises glucose.

The present application also describes the use of a food composition as described above to prevent diabetes, advantageously non-insulin-dependent diabetes, and/or to improve glucose tolerance.

Another object of the present invention relates to the non-therapeutic use of the food composition to prevent diabetes, obesity, metabolic syndrome or insulin resistance related to aging and/or to improve glucose tolerance.

Advantageously, the inventive food composition comprises glucose and is used, non-therapeutically, as an energy foodstuff such as, for example, an energy drink.

The combined presence of chicoric acid and/or at least a metabolite thereof, in particular monocaffeoyl-tartaric acid and/or m-hydroxyphenylpropionic acid, and/or 4-vinylcathecol and/or 4-ethylcatechol, with glucose improves the availability of said glucose to the consumer's body, in particular to the consumer's muscles.

LEGEND OF FIGURES

FIG. 1: Demonstration of the direct insulin stimulating effect of chicoric acid (SAT2) on isolated INS-1E β cells.

Figure 2:
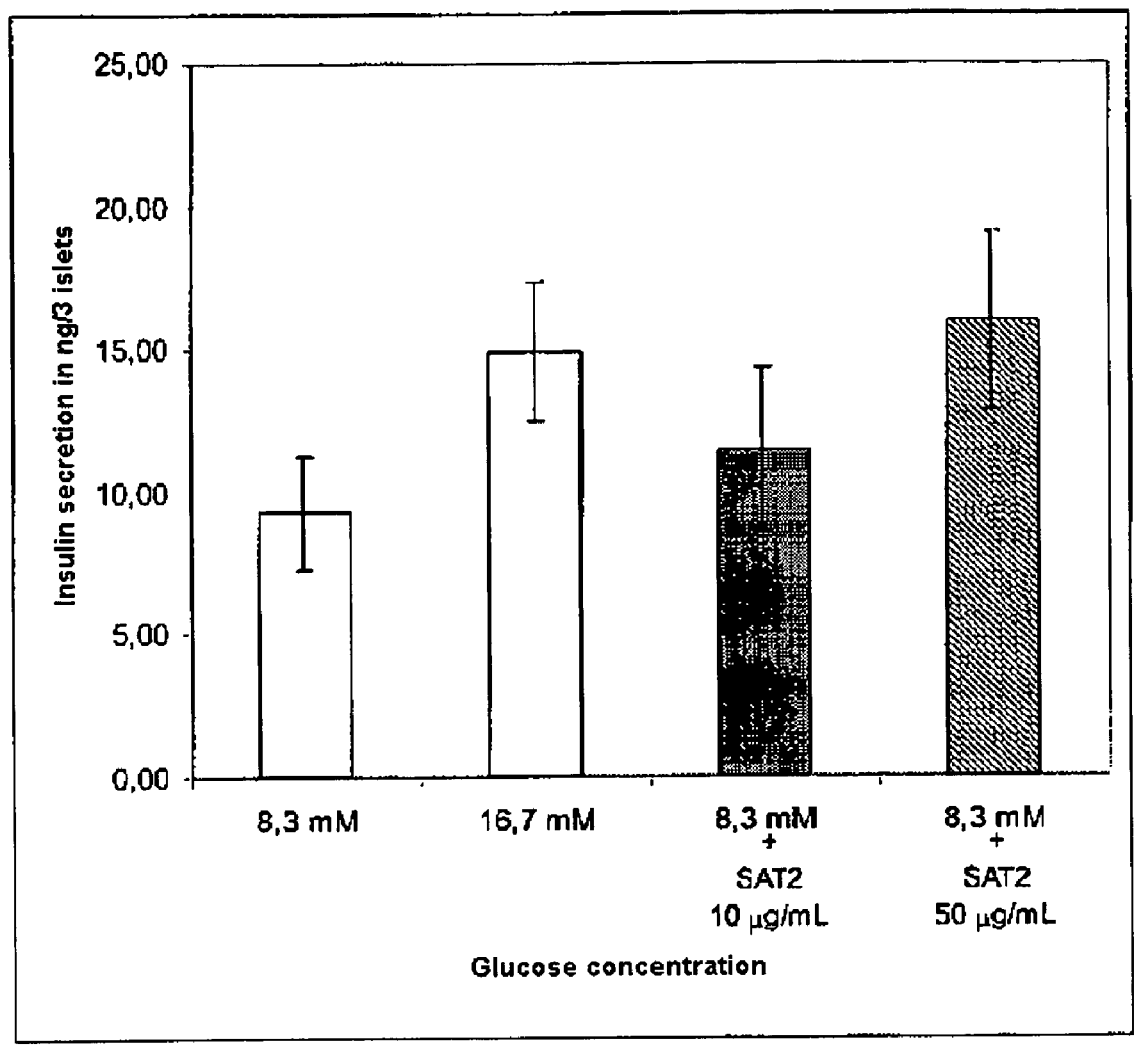

FIG. 2: Insulin stimulating effect of chicoric acid (SAT2) on incubated isolated rat islets of Langerhans.

Figure 3:
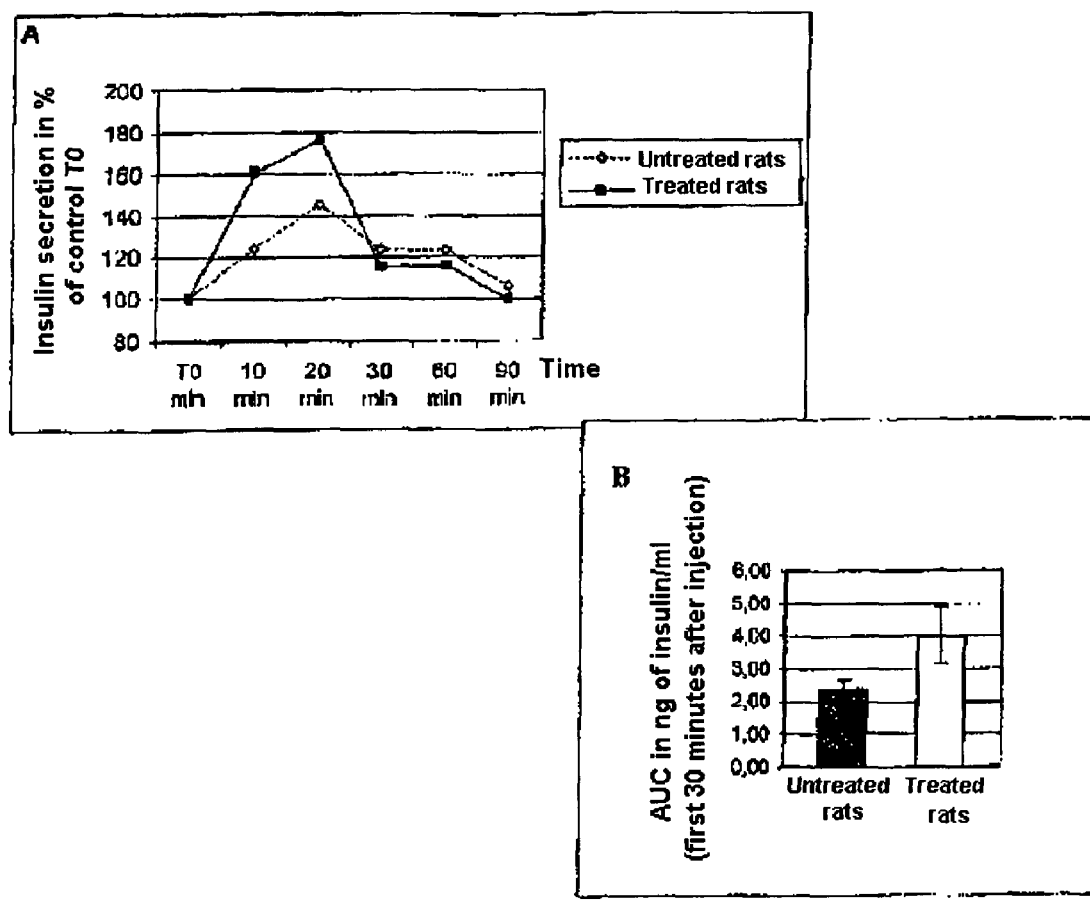

FIG. 3: Effect of intraperitoneal (IP) injection of chicoric acid (SAT2) during a test of induced hyperglycemia (1 g/kg IP) in normal awake rats.

A—Kinetics of insulinemia after injection.

B—Area under the curve (AUC) for insulinemia during the first 30 minutes after injection.

Each kinetics graph represents a mean of 8 animals.

Figure 4:
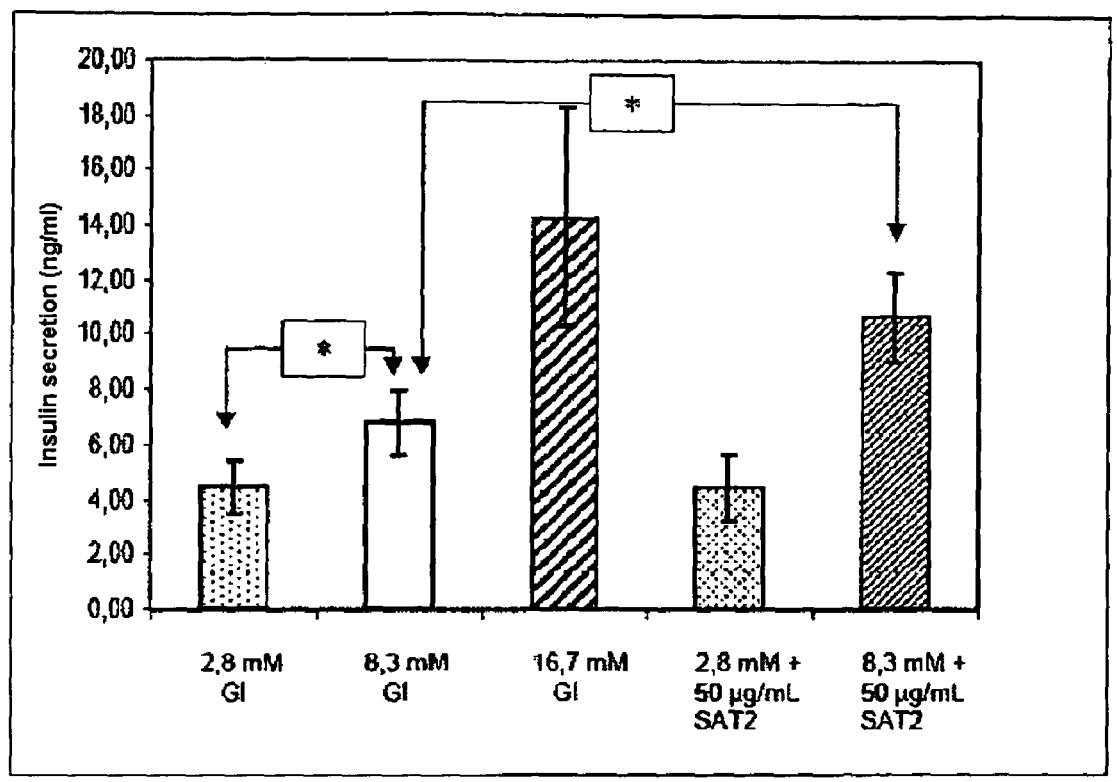

FIG. 4: Effect of SAT2 on insulin secretion in islets of Langerhans isolated from rat pancreas.

Figure 5:
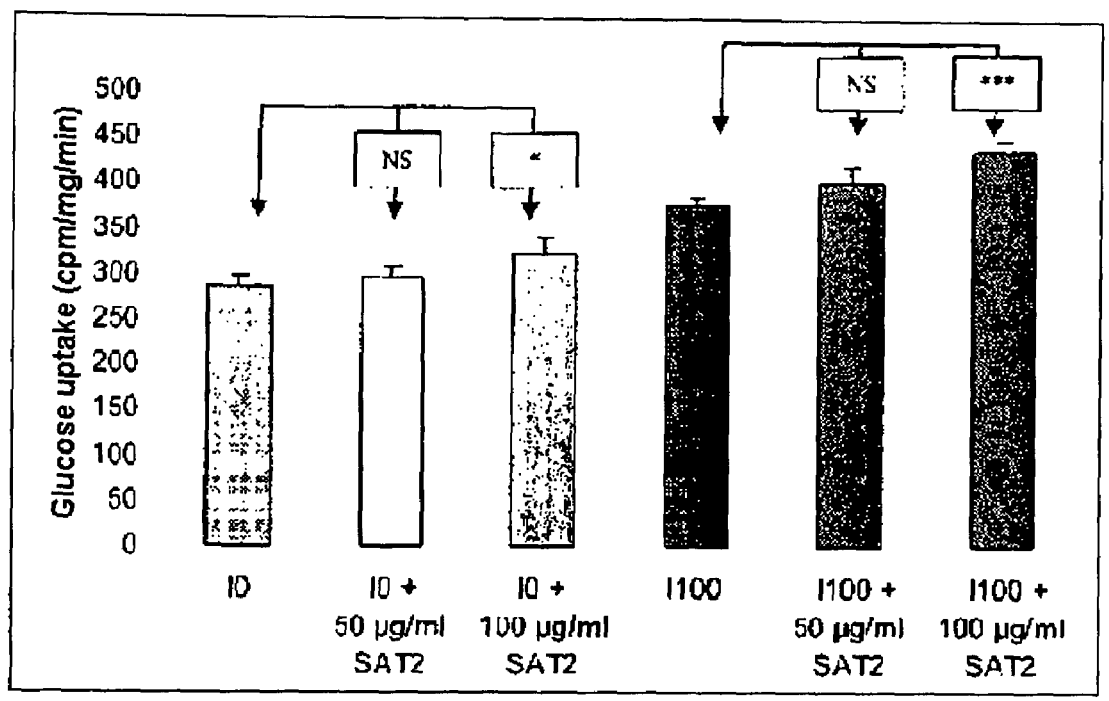

FIG. 5: Effects of SAT2 on glucose capture in the presence or absence of insulin in the L6 rat myocyte cell line.

EXAMPLES

The chicoric acid obtained by the method described above (called SAT2 in our examples) is used for pharmacological tests to objectify insulin stimulating activity with antidiabetic potential. These tests were carried out in vitro on pancreatic β cell cultures from rat pancreas and on islets of Langerhans isolated from rat pancreas as well as in vivo in the rat.

In the examples presented below, the concentration of insulin secreted was evaluated by a quantification system developed by Cis Bio International and the inventors using the FRET principle (9): Insulin Kit.

Glycemia was analyzed by an enzymatic method using a commercial kit (Boehringer, Mannheim, Germany). The results were subjected to an analysis of variance followed by a multiple comparison test.

Example 1

Investigation in Cultured β Cells (FIG. 1)

The cultured β cells are INS-1E cells from rat insulinoma cultured in complete RPMI 1640 media. The significance of these cells is that they increase their secretion of insulin according to the concentration of glucose in the medium (10), even if the latter are completely disconnected from their physiological environment. The cells are cultivated in RPMI medium with 10% fetal calf serum (FCS) and 11 mM glucose (supplemented with 100 μg each penicillin and streptomycin (antibiotics), 50 μM β-mercaptoethanol and 1 mM sodium pyruvate).

Four days after inoculating the cells on 24-well plates, the culture medium is discarded and replaced by RPMI medium+ 10% FCS without glucose. The cells are returned to incubate at 37° C. for 12 hours. Washed twice with 1 ml of Krebs-Ringer solution without glucose, the cells are placed for 90 minutes in Krebs-Ringer solution enriched in glucose with or without SAT2 (at concentrations of 10-50 μg/ml).

FIG. 1 shows that the INS-1E cells used are perfectly functional since an increase in glucose concentration from 3 mM to 5 mM in the culture medium stimulates insulin secretion in these cells by +89% ($p<0.01$).

In accordance with the present invention, this experiment shows that adding 10 μg/ml (24.5 μM) of SAT2 in the medium containing 3 mM glucose (90 minutes of incubation) significantly increases insulin secretion (+81%, $p<0.01$). On INS-1E cells, such a stimulation of insulin secretion induced by SAT2 in the presence of 3 mM glucose is equivalent to that obtained on these cells during the increase in glucose from 3 mM to 5 mM. An equivalent stimulation of insulin secretion is obtained in a medium with 3 mM glucose but in the presence of 50 μg/ml (122 μM) of SAT2, which is a concentration five times higher than the preceding experiment; this suggests that SAT2 very quickly reached a maximum stimulation which is much lower than the stimulation obtained in the presence of 200 μM of tolbutamide (sulfonylurea), the concentration typically used.

This stimulation of insulin secretion by SAT2 should avoid hypoglycemia, a side effect frequently observed during treatment with sulfonylureas.

Example 2

Investigation in Islets of Langerhans Isolated from Rat Pancreas from (FIG. 2)

Islets of Langerhans constitute the endocrine part of the pancreas and contain primarily β cells which secrete insulin. Islets of Langerhans of rat pancreas are isolated by digestion of the pancreas using collagenase according to a method adapted from that of Lacy et al. (11).

The islets were separated from the other elements of the digestate, taken under a binocular magnifier and then deposited in incubation tubes. On normal Wistar rat islets incubated in Krebs-Ringer buffer with or without SAT2 in the presence of 8.3 mM glucose for one hour, the effect of various concentrations of chicoric acid on insulin secretion was investigated.

It was verified that the islets obtained were functional since the increase in the concentration of glucose (from 8.3 mM to 16.7 mM) induced a stimulation of insulin secretion (+58%, $p<0.05$). Adding a 10 μg/ml concentration of chicoric acid (SAT 2) when the islets are incubated in the presence of 8.3 mM glucose triggers an increase in insulin secretion (+21%).

A greater stimulation is observed when SAT2 is added at a concentration of 50 μg/ml (+68%, $p<0.01$) for the same concentration of glucose (8.3 mM).

This adding of chicoric acid causes a rise in insulin secretion similar to that obtained during the increase in glucose alone (to 16.7 mM).

Example 3

Experiment in Normal Awake Wistar Rats (FIG. 3)

The effect of administering chicoric acid in the rat was tested during an induced hyperglycemia test (1 g glucose/kg live weight). The animals received a single intraperitoneal injection, either glucose alone or glucose plus chicoric acid at a concentration of 5 mg/kg live weight.

Our results show that adding chicoric acid to the glucose improves the animals' insulin response to glucose. This increase in hyperinsulinemia caused by sugar appears during the first 30 minutes after injection. Calculation of the area under the curve (AUC) during these 30 minutes reveals a clearly greater stimulation of insulin secretion in the presence of chicoric acid (SAT2) ($p<0.01$).

Example 4

Investigation of the Insulin Stimulating Effect of SAT2 According to Glucose Concentration in Islets of Langerhans Isolated from Rat Pancreas (FIG. 4)

After digestion of the pancreas by the enzymatic method with collagenase, the islets were separated from the other elements of the digestate, taken under a binocular magnifier and then deposited in incubation tubes. On normal Wistar rat islets incubated in Krebs-Ringer buffer in the presence of a 2.8 mM, 8.3 mM and 16.7 mM concentration of glucose for one hour, the effect of 50 μg/ml chicoric acid on insulin secretion by islets stimulated by 2.8 mM and 8.3 mM of glucose was investigated.

After incubating for 1 hour 3 isolated islets of Langerhans in the presence of various concentrations of glucose (Gl) with or without a concentration of 50 μg/ml SAT2, the samples were analyzed.

The results obtained are presented in FIG. 4 and table 2 below.

The results presented are the mean of 6 points/test and 3 independent tests (*, $P<0.05$).

TABLE 2

|  | Quantity of insulin secreted in ng (mean of 18 independent tests) | Standard deviation |
|---|---|---|
| 2.8 mM Gl | 4.45 | 0.95 |
| 8.3 mM Gl | 6.79 | 1.2 |
| 16.7 mM Gl | 14.32 | 3.97 |
| 2.8 mM Gl + 50 μg/ml SAT2 | 4.44 | 1.22 |
| 8.3 mM Gl + 50 μg/ml SAT2 | 10.65 | 1.62 |

Considering this table and FIG. 4, it can be observed that under a low concentration of glucose (2.8 mM), SAT2 does not stimulate insulin secretion in islets of Langerhans. When the glucose concentration is high (8.3 mM), an increase in insulin secretion is observed (+52%, $p<0.05$, Student's t-test). The presence of SAT2 with 8.3 mM glucose highly significantly stimulates insulin secretion (+56%, $p<0.05$, Student's t-test). Thus, these results show that chicoric acid (SAT2) has a glucose-dependent modulating effect on insulin secretion by islets of Langerhans.

This example shows that the insulin stimulating effect of chicoric acid is dependent on glucose concentration. This is an important result since it shows that SAT2 (chicoric acid) is able to stimulate insulin secretion without causing hypoglycemia in the patient as sometimes occurs with patients treated by sulfonylureas, a situation that can be dangerous particularly in the elderly.

Example 5

Effects of SAT2 on Glucose Uptake in the Presence or Absence of Insulin in the L6 Rat Myocyte Cell Line (FIG. 5)

To demonstrate the stimulating effect of chicoric acid on glucose uptake at a stimulating concentration of insulin, the myocyte cell line model was selected. The L6 line (a line from the skeletal muscle of Rattus norvegicus provided by ATCC-LCC Promochem) was used. Glucose uptake in the presence of insulin with or without SAT2 was quantified using [$^3$H]-deoxyglucose.

The L6 cell line is cultivated in DMEM (4.5 g/l glucose) supplemented with 10% fetal calf serum (FCS). For the glucose uptake experiments, the cells are inoculated in 12-well plates at a density of $10^4$ cells/well. After three days of culture, the cells are differentiated in DMEM with 2% FCS for one week. The day of the experiment, the cells are deprived for 4 hours in DMEM without FCS and containing 0.1% BSA, and then they are incubated for 1 hour in a Krebs-Ringer buffer containing 1 g/l glucose and containing 0.100 nM and 500 nM insulin with or without SAT2 at a concentration of 50 µg/ml or 100 µg/ml. The cells are then washed in Krebs-Ringer and then incubated in the presence of 0.5 µCi [$^3$H]-deoxyglucose in 1 ml Krebs-Ringer per well. Glucose uptake by the L6 cells is stopped by three washings in cold PBS and the cells are then lysed in 1 ml of a 0.1 N NaOH solution. Concentration in total protein is estimated by the Bradford method and radioactivity is measured using a β counter. The final results are expressed in cpm/mg/min. The Student's t-test is used to analyze statistical significance.

After one week of differentiation, the cells are stimulated for 1 hour in the absence (I0) and in the presence (I100) of 100 nM insulin combined with increasing concentrations of SAT2 (50 µg/ml and 100 µg/ml). The effects on glucose uptake are measured in the presence of [$^3$H]-deoxyglucose for 5 minutes. (*, $p<0.05$; ***, $p<0.001$; NS, not significant).

Result: this example shows that SAT2 has a significant insulin sensitizing effect on the L6 line in culture. In the absence of insulin, SAT2 significantly stimulates glucose uptake only at the highest concentration of 100 µg/ml (+12.7%, $p<0.05$). Insulin at 100 Nm increases glucose capture by 30.4% ($p<0.001$). Adding 100 µg/ml SAT2 amplifies glucose uptake by 16.3% ($p<0.001$). The SAT2 molecule is thus able to stimulate glucose uptake in a rat myocyte cell line. A large part of this effect is independent of the presence of insulin (approximately 12%). Roughly 4% of the effect is nevertheless dependent on insulin and its signaling pathway.

REFERENCES (1) Zimmet P., K G. Alberti, and J. Shaw. Global and societal implications of the diabetes epidemic. *Nature* 414: 782-787, 2001.
(2) Broca C., R. Gross, P. Petit, Y. Sauvaire, M. Manteghetti, M. Tournier, P. Masiello, R. Gomis and G. Ribes. 4-Hydroxyisoleucine: experimental evidence of its insulinotropic and antidiabetic properties. *The American Physiological Society* E617-623, 1999.
(3) Hemmerle H., H.-J. Burger, P. Below, G. Schubert, R. Rippel, P. W. Schindler, E. Paulus and A. W. Herling. Chlorogenic acid and synthetic chlorogenic acid derivatives: novel inhibitors of hepatic glucose-6-phosphate translocase. *J Med. Chem,* 40, 137-145, 1997.
(4) King P. J., G. Ma, W. Mia, Q. Jia, B. R. McDougall, M. G. Reinecke, C. Cornell, J. Kuan, T. R. Kim, W. E. J. R. Robinson, K. Zhu, M. L. Cordeiro, J. Atienza, S. A. Chow, H. H. Lo, J. G. Chung, R. Ejzemberg, M H. Da Silva, L. Pinto, W B. Mors, Y. Jiang, K. Satoh, K. Kusama, S. Watanabe and H. Sakamagi, Structure-activity relationships: analogues of the dicaffeoylquinic and dicaffeoyltartric acids as a potent inhibitors of human immunodeficiency virus type 1 integrase and replication. *J. Med. Chem.,* 42: 497-509, 1999.
(5) Facino R. M., M. Carini, G. Aldini, L. Saibene, P. Pietta and P. Mauri. Echinacoside and caffeoyl conjugates protect collagen from free radical-induced degradation: a potential use of *Echinacea* extracts in the prevention of skin photodamage. *Planta Med.* 61:510-514, 1995.
(6) Dalby-Brown L, H. Barsett, A. K. Landbo, A. S. Meyer and P. Molgaard. Synergistic antioxidative effects of alkamides, caffeic acid derivatives, and polysaccharide fractions from *Echinacea purpurea* on in vitro oxidation of human low-density lipoproteins. *J Agric Food Chem.,* November 30; 53(24):9413-23, 2005.
(7) Zaho H. and T R. Burke. Facile syntheses of (2R,3R)-(−)- and (2S,3S)-(+)-chicoric acids. *Synthetic Communications,* 28:737-740, 1998.
(8) Scarpati M L. and G. Oriente. Chicoric acid (dicaffeoyltartric acid): its isolation from chicory (*Cichorium intybus*) and synthesis. *Tetrahedron,* 4:43-48, 1958.
(9) Claret E. et al., abstract, conference The Society for Biomolecular Screening, September 11-15, Orlando, Fla., 2004.
(10) Sekine N, Fasolato C, Pralong W F, Theler J M, Wollheim C B. Glucose-induced insulin secretion in INS-1 cells depends on factors present in fetal calf serum and rat islet-conditioned medium. *Diabetes* 46(9): 1424-33, 1997.
(11) Lacy P. E., and M. Kostianovsky. Method for the isolation of intact islets of Langerhans from the rat pancreas. *Diabetes* 16: 35-39, 1967.

The invention claimed is:

1. A method for treating insulin resistance or hypoinsulinemia and/or associated pathologies selected from the group consisting of diabetes, dyslipidemia, in particular hyperlipidemia and hypertriglyceridemia, metabolic syndrome, arterial hypertension and obesity, comprising administering an effective amount of a composition comprising chicoric acid and/or at least one metabolite thereof chosen among mono-caffeoyl-tartaric acid and/or m-hydroxyphenylpropionic acid, and/or 4-vinylcathecol and/or 4-ethylcatechol to a subject in need thereof.

2. The method according to claim 1, wherein the composition is insulin stimulating and wherein the method is for treating hypoinsulinemia.

3. The method according to claim 1, wherein the pathology is diabetes.

4. The method according to claim 3, wherein the diabetes is non-insulin-dependent diabetes.

5. The method according to claim 3, wherein the diabetes is insulin-dependent diabetes.

6. The method according to claim 2, wherein the insulin stimulating activity of the composition is dependent on the concentration of glucose in the blood of the subject.

7. The method according to claim 6, wherein the composition is insulin stimulating in a subject with a blood glucose concentration greater than 1 g/l.

8. The method according to claim 1, wherein the composition is insulin sensitizing.

9. The method according to claim 1, wherein the chicoric acid and/or monocaffeoyl-tartaric acid and/or m-hydroxyphenylpropionic acid, and/or 4-vinylcathecol and/or 4-ethylcatechol is of natural or synthetic origin.

10. The method according to claim 9, wherein the chicoric acid and/or monocaffeoyl-tartaric acid and/or m-hydroxyphenylpropionic acid, and/or 4-vinylcathecol and/or 4-ethylcatechol is of plant origin.

11. The method according to claim 10, wherein the chicoric acid and/or at least one metabolite thereof chosen among monocaffeoyl-tartaric acid and/or m-hydroxyphenylpropionic acid, and/or 4-vinylcathecol and/or 4-ethylcatechol is obtained from plants belonging to the family of Asteraceae, Lamiaceae, Fabaceae, Equisetaceae or Potamogetonaceae.

12. The method according to claim 1, wherein the chicoric acid and/or monocaffeoyl-tartaric acid and/or m-hydroxyphenylpropionic acid, and/or 4-vinylcathecol and/or 4-ethylcatechol are obtained from wild or cultivated chicories.

13. The method according to claim 1, comprising administering 5-30 mg/kg of chicoric acid and/or less than 5-30 mg/kg of monocaffeoyl-tartaric acid and/or m-hydroxyphenylpropionic acid, and/or 4-vinylcathecol and/or 4-ethylcatechol and/or caffeic acid, and/or tartaric acid, and/or ferulic acid and/or dihydrocaffeic acid, per dose.

14. A method for preventing insulin resistance or hypoinsulinemia and/or associated pathologies selected from the group consisting of diabetes, dyslipidemia, in particular hyperlipidemia and hypertriglyceridemia, metabolic syndrome, arterial hypertension and obesity, comprising administering an effective amount of a composition comprising chicoric acid and/or at least one metabolite thereof chosen among monocaffeoyl-tartaric acid and/or m-hydroxyphenylpropionic acid, and/or 4-vinylcathecol and/or 4-ethylcatechol to a subject in need thereof.

15. The method according to claim 14, wherein the composition is insulin stimulating and wherein the method is for preventing hypoinsulinemia.

16. The method according to claim 14, wherein the pathology is diabetes.

17. The method according to claim 16, wherein the diabetes is non-insulin-dependent diabetes.

18. The method according to claim 16, wherein the diabetes is insulin-dependent diabetes.

19. The method according to claim 15, wherein the insulin stimulating activity of the composition is dependent on the concentration of glucose in the blood of the subject.

20. The method according to claim 19, wherein the composition is insulin stimulating in a subject with a blood glucose concentration greater than 1 g/l.

21. The method according to claim 14, wherein the composition is insulin sensitizing.

22. The method according to claim 14, wherein the chicoric acid and/or monocaffeoyl-tartaric acid and/or m-hydroxyphenylpropionic acid, and/or 4-vinylcathecol and/or 4-ethylcatechol is of natural or synthetic origin.

23. The method according to claim 22, wherein the chicoric acid and/or monocaffeoyl-tartaric acid and/or m-hydroxyphenylpropionic acid, and/or 4-vinylcathecol and/or 4-ethylcatechol is of plant origin.

24. The method according to claim 23, wherein the chicoric acid and/or at least one metabolite thereof chosen among monocaffeoyl-tartaric acid and/or m-hydroxyphenylpropionic acid, and/or 4-vinylcathecol and/or 4-ethylcatechol is obtained from plants belonging to the family of Asteraceae, Lamiaceae, Fabaceae, Equisetaceae or Potamogetonaceae.

25. The method according to claim 14, wherein the chicoric acid and/or monocaffeoyl-tartaric acid and/or m-hydroxyphenylpropionic acid, and/or 4-vinylcathecol and/or 4-ethylcatechol are obtained from wild or cultivated chicories.

26. The method according to claim 14, comprising administering 5-30 mg/kg of chicoric acid and/or less than 5-30 mg/kg of monocaffeoyl-tartaric acid and/or m-hydroxyphenylpropionic acid, and/or 4-vinylcathecol and/or 4-ethylcatechol and/or caffeic acid, and/or tartaric acid, and/or ferulic acid and/or dihydrocaffeic acid, per dose.

* * * * *